US005652653A

United States Patent [19]
Alsmeyer et al.

[11] Patent Number: 5,652,653
[45] Date of Patent: *Jul. 29, 1997

[54] ON-LINE QUANTITATIVE ANALYSIS OF CHEMICAL COMPOSITIONS BY RAMAN SPECTROMETRY

[75] Inventors: Daniel Charles Alsmeyer, Kingsport; Michael Joseph Pearce, Blountville; Vincent Alvin Nicely, Kingsport, all of Tenn.

[73] Assignee: Eastman Chemical Company, Kingsport, Tenn.

[*] Notice: The term of this patent shall not extend beyond the expiration date of Pat. No. 5,455,673.

[21] Appl. No.: 703,281

[22] Filed: Aug. 26, 1996

Related U.S. Application Data

[60] Division of Ser. No. 450,598, May 25, 1995, which is a continuation-in-part of Ser. No. 250,396, May 27, 1994, Pat. No. 5,455,673.

[51] Int. Cl.$^6$ .............................. G01J 3/44; G01N 21/65
[52] U.S. Cl. .................................................. 356/301
[58] Field of Search ................................. 356/301

[56] References Cited

U.S. PATENT DOCUMENTS

| | | | |
|---|---|---|---|
| 3,033,822 | 5/1962 | Kibler et al. . | |
| 3,556,659 | 1/1971 | Hawes | 356/301 |
| 3,772,405 | 11/1973 | Hamb . | |
| 4,259,478 | 3/1981 | Jackson, Jr. et al. . | |
| 4,573,761 | 3/1986 | McLachlan et al. | 356/301 |
| 4,620,284 | 10/1986 | Schnell et al. | 356/301 |
| 5,112,127 | 5/1992 | Carrabba et al. | 356/301 |
| 5,455,673 | 10/1995 | Alsmeyer et al. | 356/301 |

FOREIGN PATENT DOCUMENTS

| | | |
|---|---|---|
| 2571144 | 4/1986 | France . |
| WO87/06011 | 10/1987 | WIPO . |

OTHER PUBLICATIONS

Odian, *Principles of Polymerization*, 3rd ed., Wiley, New York, 1991, pp. 97–100.
Billmeyer, *Textbook of Polymer Science*, 3rd ed., Wiley, New York, 1984, pp. 442–445.
Wang and McCreery, *Anal. Chem.*, 1990, vol. 62, pp. 2647–2651.
Chase, *J. Am. Chem. Soc.*, 1986, vol. 108, pp. 7485–7488.
Carrabba et al., "Compact Raman Instrumentation for Process adn Environmental Monitoring," SPIE, 1991, vol. 1434, pp. 127–134.

(List continued on next page.)

*Primary Examiner*—F. L. Evans
*Attorney, Agent, or Firm*—Cheryl J. Tubach; Harry J. Gwinnell

[57] ABSTRACT

A method for quantitatively monitoring in situ by Raman spectrometry one or more selected constituents of a chemical composition comprises: simultaneously irradiating with a substantially monochromatic radiation source a reference material and a chemical composition containing one or more constituents, the radiation being transmitted from the source to the chemical composition by an excitation conduit connecting the source to an optical probe that interfaces with the composition; simultaneously acquiring at more than one wavelength convolved Raman spectra of the reference material and the chemical composition by means of a spectrograph, which is connected to the optical probe by a collection conduit; choosing the standard Raman spectrum of the reference material; determining the convolution function of the convolved spectra from the convolved Raman spectrum and the standard Raman spectrum of the reference material; applying the convolution function to adjust the convolved Raman spectrum of the composition to produce the standard Raman spectrum of the chemical composition; and applying predetermined calibration means to the standard Raman spectrum of the chemical composition, by which the chemical constitution of the composition at the time of acquisition of the convolved Raman spectra can be ascertained.

6 Claims, 5 Drawing Sheets

OTHER PUBLICATIONS

Carrabba et al., *Appl. Spec.*, 1990, vol. 44, pp. 1558–1561.

Vess and Angel, "Near-Visible Raman Instrumentation for Remote Multi-Point Process Monitoring Using Optical Fibers and Optical Multiplexing," SPIE, 1992, vol. 1637, pp. 118–125.

Angel et al., "Simultaneous Multi-Point Fiber-Optic Raman Sampling for Chemical Process Control Using Diode Lasers and a CCD Detector," SPIE, 1991, vol. 1587, pp. 219–231.

Newman et al., *Appl. Spec.*, 1992, vol. 46, pp. 262–265.

Seasholtz et al., *Appl. Spec.*, 1989, vol. 43, pp. 1067–1972.

Allred and McCreery, *Appl. Spec.*, 1990, vol. 44, pp. 1229–1231.

Schwab and McCreery, *Anal. Chem.*, 1984, vol. 56, pp. 2199–2204.

Schoen et al., *Appl. Opt.*, 1992, vol. 36, pp. 7707–7715.

Schoen et al., SPIE, 1993, vol. 1857, pp. 116–125.

Garrison, SPIE, 1992, vol. 1681, pp. 291–293.

Bulkin et al., *Macromolecules*, 1987, vol. 20, pp. 830–835.

Bower et al., *Polymer*, 1982, vol. 23, pp. 645–649.

Adar et al., *Polymer*, 1985, vol. 26, pp. 1935–1943.

DeBlase et al., *J. Polym. Sci.*, 1985, vol. 23, pp. 109–115.

Grasselli and Bulkin, eds., "Analytical Raman Spectrometry," vol. 14, *Chem. Anal.*, 1991, Wiley, New York, pp. 223–252.

W. H. Press et al., *Numerical Recipes: The Art of Scientific Computing*, 1986, Cambridge University Press, pp. 77–89, pp. 407–412.

Savitsky et al., *Anal. Chem.*, 1964, vol. 36, pp. 1627–1639.

Takeuchi et al., *Appl. Spec.*, 1993, vol. 47, pp. 129–131.

Martens et al., *Multivariate Calibration*, 1989, Wiley, New York, pp. 1–6, 11–22, 25–30, 73–78, 116–125.

ON-LINE QUANTITATIVE ANALYSIS OF CHEMICAL COMPOSITIONS BY RAMAN SPECTROMETRY

CROSS-REFERENCE TO RELATED APPLICATION

This is a divisional application of application Ser. No. 08/450,598, filed May 25, 1995, which is a continuation-in-part of Ser. No. 08/250,396 filed May 27, 1994, now U.S. Pat. No. 5,455,673.

FIELD OF THE INVENTION

This invention relates to Raman spectrometric analysis, and more particularly a method for quantitatively monitoring in situ by Raman spectrometry constituents of a chemical composition.

BACKGROUND OF THE INVENTION

The use of spectrometry in analytical laboratories for measuring physical and analytical properties of materials is a well established art. Raman spectrometry is one such technique that can provide qualitative and quantitative information about composition and/or molecular structure of chemical substances. When incident radiation interacts with matter it may undergo a process called scattering. Scattered radiation may be elastic, in which the incident wavelength is unchanged in the scattered radiation, or inelastic, in which the scattered radiation has different wavelengths than the incident radiation. In one form of inelastic radiation scatter, referred to as Raman scattering, incident photons are scattered with either a gain or loss of energy. The energy difference between the scattered and incident radiation is commonly referred to as the Raman shift. The resultant Raman shift spectrum provides the energy of various molecular vibrational motions and conveys chemical and molecular information regarding the matter studied. The Raman scattering effect is extremely weak; typically a few Raman scattered photons exist among millions of elastically scattered photons.

Determining the constitution of a chemical composition or monitoring the progress of a chemical reaction is frequently carried out with materials situated in inhospitable environments. Analyses of process streams under conditions of high temperature and/or pressure or in the presence of corrosive substances or powerful solvents are often required. It may be necessary, for example, to follow the progress of a reaction forming polymers from lower molecular weight reactants in a high temperature continuous or batch process. Similarly, it may be desirable to monitor as a function of time the composition of batch reactions or volatile materials at a distillation head. Spectrophotometric apparatus such as a spectrograph and a radiation source can be situated in a location remote from materials such as polymer-forming compositions and distillation mixtures that are to be analyzed in situ, the sampling site being connected to the apparatus by radiation conduits comprising optical fibers.

Of course, the method of the present invention is not limited to use only in harsh environments characterized by, for example, higher temperatures. Quantitative in situ Raman spectrometric measurements in accordance with the invention may be carried out, assuming the availability of suitable optical probes, in diverse environments, including living organisms.

A polyester is a synthetic resin that contains ester linkages in the main polymer chain. Commercially valuable polyesters, useful for clothing fibers, container packaging, etc., are manufactured from various reactants. For example, they may be produced by esterification of dicarboxylic acids with diols, transesterification of dicarboxylic esters with diols, or self-condensation of hydroxycarboxylic acids.

Achieving particular end-use properties of a polyester requires vigorous control of the component ratios or composition of the materials in the reaction vessel during manufacture. Small changes in initial composition can dramatically affect the usefulness of the final polyester product. Control of the conversion of the ester or acid end groups, depending on the use of diesters or diacids, to the reactive hydroxy end groups is also required to ensure reliable finished polyester product characteristics. Low conversion during the first stage reaction limits the reactivity during the polycondensation reaction and adversely affects the ultimate end use properties of the polyester material. For this reason, it is extremely important to know the conversion or extent of the first stage reaction. Other critical composition control parameters include the amounts of each diacid and diol moiety, the ratio of total diols to total diacids and/or diesters in the reaction vessel, and the degree of polymerization, molecular weight, or size of the polymer chain.

During manufacturing, the chemical constitution of materials in the reaction vessels may be determined by removing a small sample for analytical testing in a remote laboratory. Commonly used analytical methods may be used to provide an indication of the extent of the first stage reaction, molar amounts of reactants and products in the mixture, and the extent of reaction. Laboratory methods commonly used to obtain compositional information of the extracted samples include nuclear magnetic resonance (NMR) spectrometry, gas chromatography (GC), and liquid chromatography (LC). These methods require the extracted sample to be dissolved and in some cases derivatized. NMR methods provide reliable information; however, the required instrumentation is expensive and complex and the sample must be properly prepared prior to measurement.

PROBLEMS TO BE SOLVED BY THE INVENTION

Repetitious sampling and analytical measurements applied to a chemical production process present several significant potential problems.

First, there is the inherent danger of removing a sample from a hot process stream, especially when the stream is viscous as in a polymer-forming process. Large insulated valves must be opened to allow material to flow into a small sample container. It is not uncommon for sampling ports in polymer lines to become partially plugged, causing the hot material to be unpredictably expelled from the opening.

Second, the procedure of removing a sample may alter the sample constitution. For example, the first stage reaction in one common polyester manufacturing process is usually performed with an excess of ethylene glycol (EG) in the reactor. EG is more volatile than the oligomeric material and, when removed from the process, may preferentially flash from the sample, resulting in a non-representative sample. Furthermore, as the sampled material is viscous, it clings to the sample port valve, which may cause the current sample to be intermixed with remnants of previously acquired samples.

Third, the sampling and analysis procedure is time-consuming. Many thousands of pounds of material can be produced in the time required to remove, prepare, and analyze a sample. The analytical data obtained from the sample is therefore of limited value for proactive process control.

Finally, because of the difficulties and cost associated with the hazards of sample removal, analytical sampling is typically infrequent. With minimal analytical data points, it is difficult to gain a statistically valid understanding of process variations or to make proper control adjustments to the process.

A preferred analysis method would monitor the material as it is being produced. Such a method would reduce the need to remove samples from the production environment, diminish the safety concerns, and facilitate more frequent and faster measurements.

There are, however, challenging obstacles that prevent most analytical techniques from providing in situ, on-line chemical constitution information in a process environment. First, the analytical method must be capable of accurately determining the desired properties with sufficient precision. Second, the analytical instrument must either be capable of withstanding the physical environment of a processing area or must be capable of sensing the desired composition properties from a remote location. Third, the interface of the instrumentation with the process must be able to survive the harsh pressure and temperature environment found inside the chemical process line. Fourth, turbidity, bubbles, and other common processing phenomena must not disturb the analytical measurements. All of these obstacles are overcome by the method of the present invention.

SUMMARY OF THE INVENTION

A method for quantitatively monitoring in situ by Raman spectrometry one or more selected constituents of a chemical composition comprises: simultaneously irradiating with a substantially monochromatic radiation source a reference material and a chemical composition containing one or more constituents, the radiation being transmitted from the source to the chemical composition by an excitation conduit connecting the source to an optical probe that interfaces with the composition; simultaneously acquiring at more than one wavelength convolved Raman spectra of the reference material and the chemical composition by means of a spectrograph, which is connected to the optical probe by a collection conduit; choosing the standard Raman spectrum of the reference material; determining the convolution function of the convolved spectra from the convolved Raman spectrum and the standard Raman spectrum of the reference material; applying the convolution function to adjust the convolved Raman spectrum of the chemical composition to produce the standard Raman spectrum of the composition; and applying predetermined calibration means to the standard Raman spectrum of the chemical composition, by which the chemical constitution of the composition at the time of acquisition of the convolved Raman spectra can be ascertained.

ADVANTAGEOUS EFFECTS OF THE INVENTION

The method of the present invention is a significant improvement over traditional analytical methods, in that more reliable measurements are obtained in less time and without the difficulties of continuously removing samples. The information obtained may be used to devise feed-back or feed-forward control strategies to improve product quality, reduce waste, improve process throughputs, and lessen the hazards associated with extraction of samples from a chemical manufacturing process.

DETAILED DESCRIPTION OF THE INVENTION

Commercially useful chemicals such as polyesters, for example, are typically manufactured by large scale continuous processes at elevated temperatures. These processes for the preparation of polyesters entail esterification reactions such as the esterification of dicarboxylic acids or the transesterification of dicarboxylic esters with diol compounds.

A diol compound contains two hydroxyl functionalities. A great variety of diols can be used in the manufacture of polyesters, including, for example, ethylene glycol (EG), diethylene glycol, triethylene glycol, polyethylene glycol, polytetramethylene glycol, polypropylene glycol, polyisopropylene glycol, 1,4-butanediol, neopentyl glycol, and 1,4-cyclohexanedimethanol (CHDM).

A dicarboxylic acid contains two carboxylic acid moieties. Representative dicarboxylic acids useful in the manufacture of polyester materials include: terephthalic acid (TPA), isophthalic acid, naphthalenedicarboxylic acid, 1,4-cyclohexanedicarboxylic acid (CHDA), and various aliphatic dicarboxylic acids.

A dicarboxylic ester contains two ester functional groups. Examples of useful diesters include the esterified derivatives of any of the diacids just mentioned. An important diester that is commonly used in the manufacture of polyester materials is dimethyl terephthalate (DMT).

Figure 1:
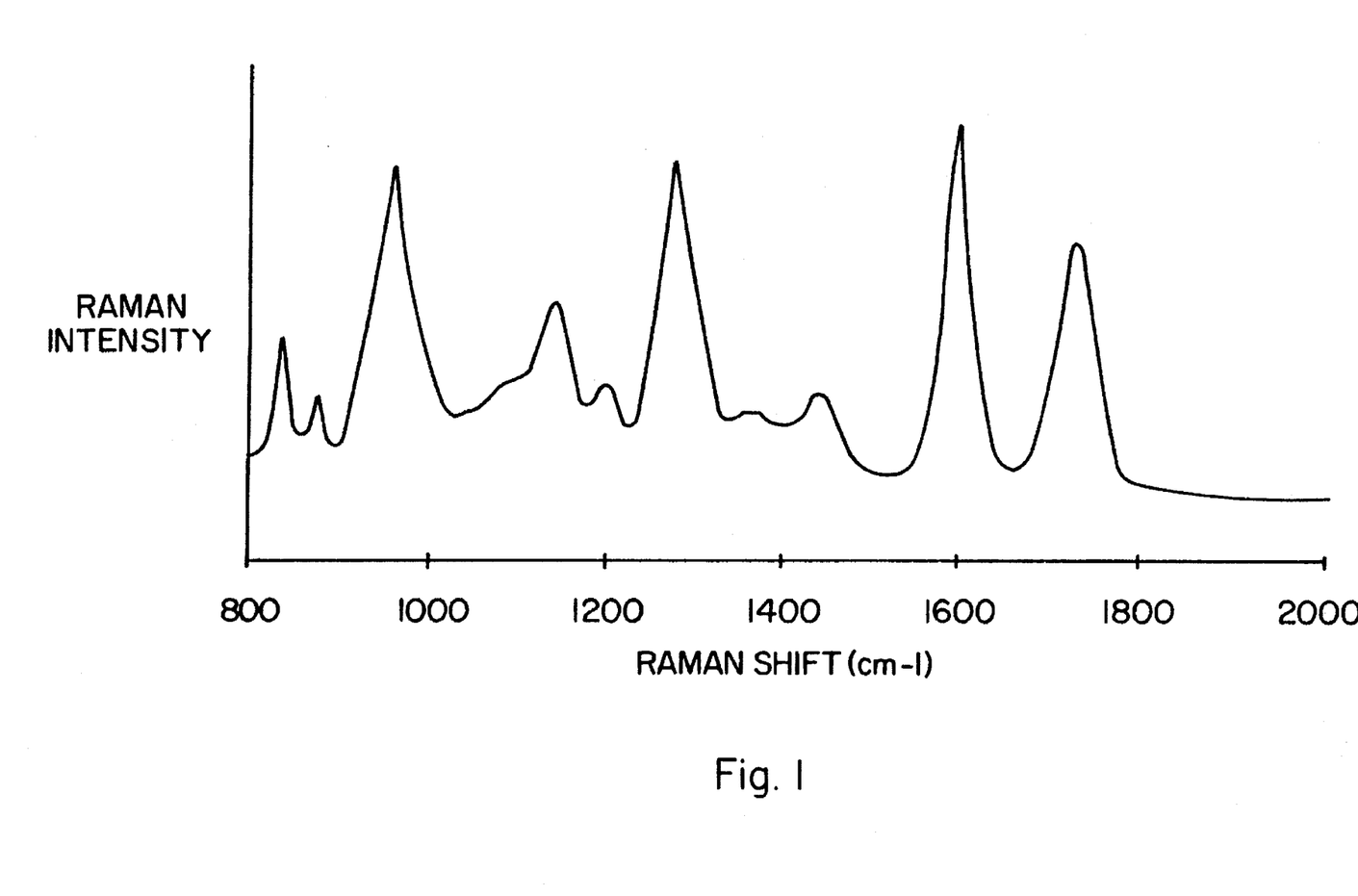
FIG. 1 is a Raman spectrum of a poly(ethylene terephthalate) intermediate.

Poly(ethylene terephthalate), PET, is an example of a commercially useful polyester. This polymer is typically manufactured from either DMT or TPA and EG, generally in two stages, as described in Odian, *Principles of Polymerization*, 3rd ed., Wiley, N.Y., 1991, pages 97 to 100, and Billmeyer, *Textbook of Polymer Science*, 3rd ed., Wiley, N.Y., 1984, pages 442 to 445, the disclosures of which are incorporated herein by reference. In the first stage, excess EG reacts with either DMT or TPA to form the intermediate bis(2-hydroxyethyl)terephthalate (BHET), whose Raman spectrum is depicted in FIG. 1. During this process, generally carried out at temperatures of 150°–230° C., methanol or water, depending on the use of DMT or TPA, respectively, is produced and continuously removed via distillation. During the second stage, referred to as the polycondensation reaction, the material is heated to temperatures of 270°–300° C. Polymerization proceeds through the removal of EG and is typically facilitated by use of a partial vacuum (0.1 to 1 torr). The polymerization process increases the molecular weight and size of the molecule, thereby altering many chemical and physical properties.

The properties of polyester materials can be modified by incorporation of different diol, diester, or diacid components in the polymer structure. For example, CHDM can be substituted for EG in the first stage reaction of PET to form a distinct polyester which has properties and end uses that differ from the EG-based product. Further, one can employ various mixtures of diols, diesters, diacids, or combinations thereof, to achieve additional polyester materials with unique properties. For example, the diols CHDM and EG may be blended in a reaction with DMT to form a glycol-modified PET. Many such modified polyesters are described in the patent literature, including U.S. Pat. Nos. 4,259,478, 3,772,405, and 3,033,822, the disclosures of which are incorporated herein by reference.

A typical Raman spectrometer is composed of a radiation source, a means of transmitting the source radiation to a sample, a means of collecting the scattered radiation from the sample, a means of energy separation, or dispersion, of the scattered radiation, and a means of detecting the radiation.

Numerous radiation sources are capable of generating Raman scatter from a material. For analytical measurement, these sources need to emit monochromatic radiation of high intensity. In this regard, lasers are well suited radiation sources. U.S. Pat. No. 3,556,659, the disclosures of which are incorporated herein by reference, describes a Raman spectrometer in which a sample contained in a tube is irradiated by radiation from a laser along the axis of the tube.

There are various classes of laser radiation sources, including: gas lasers, such as helium-neon, nitrogen, argon ion and krypton ion; solid state lasers, such as ruby lasers and Nd:YAG (neodymium:yttrium-aluminum-garnet) lasers; dye lasers; chemical lasers; and solid state lasers, such as single mode and multi-mode diode lasers.

Of these, gas lasers are generally accepted as especially suitable for dispersive Raman spectrometry because of their high degree of wavelength stability. Unfortunately, they are often expensive, require extensive maintenance, or have low output power. The use of semiconductor diode lasers in Raman spectrometry, which can provide large power output in a compact, rugged device but which may exhibit inherent instabilities in their output properties, are described in Wang and McCreery, *Anal. Chem.*, 1990, Vol. 62, pp. 2647–2651, the disclosures of which are incorporated herein by reference.

Because the Raman scattering process relates to a shift from an incident wavelength, different lasers provide spectra in different wavelength regions. However, the Raman shift spectra in those regions are similar, and essentially the same structural information can be obtained through the use of different incident laser wavelengths.

Fluorescence is a process by which absorbed radiation induces broad emission, characteristic of the molecular structure. The induced fluorescence signal, if observed, is typically many orders of magnitude larger than the Raman signal and in some cases completely masks the Raman shift spectrum. Thus, it is desirable to select an incident wavelength that minimizes fluorescence emission processes.

A well known method to reduce fluorescence background problems is to use lasers which generate red or near infrared radiation, with wavelengths from about 660 nanometers to 1100 nanometers, as described in D. B. Chase, *J. Am. Chem. Soc.*, 1986, Vol. 108, pp. 7485–7488, the disclosures of which are incorporated herein by reference. Such a method is useful because the fluorescence emission profile is independent of incident wavelength and the Raman process is a shift from the incident wavelength. Typical radiation sources operating in this region include krypton ion gas lasers, single mode diode lasers, multi-mode diode lasers, and Nd:YAG lasers.

Of the numerous radiation sources available, lasers are highly preferred because of their powerful, monochromatic radiation characteristics. Of the various types of lasers that are commercially available, diode lasers are preferred because of the minimal maintenance required over their extended useful lifetimes. This advantage is very desirable in a component for process analyzer instrumentation. Further, it is highly preferred to utilize a laser which is pre-coupled to a fiber optic cable. Fiber coupled diode laser devices, referred to as pigtailed diode lasers, are commercially available.

A pigtailed diode laser provides several substantial advantages over other laser sources. First, they are already coupled to a fiber optic cable, which eliminates complex optical alignment mechanisms that can become unfocused and cause loss of signal. This simplicity allows for easy removal and replacement when necessary. In addition, a diode laser typically has a long lifetime of usefulness, thus requiring only minimal maintenance. Furthermore, a diode laser is temperature tunable over a small wavelength range, which provides a compensation means for any slight wavelength drift that may occur. Finally, diode lasers are available with high power, making possible a greater signal and, consequently, a shorter measurement time. A concern with higher powered diode lasers is that they operate in what is called "multimode", wherein many lasing modes are all simultaneously active. These individual modes are unstable with respect to one another and can render the device useless for precise quantitative analytical measurements. Instabilities in diode lasers may be reduced but not completely eliminated through proper control of temperature and unwanted emissions, as described in Carrabba et al., "Compact Raman Instrumentation for Process and Environmental Monitoring," SPIE, 1991, Vol 1434, *Environmental Sensing and Combustion Diagnostics*, pp. 127–134, the disclosures of which are incorporated herein by reference. For the control of undesirable laser emissions, Carrabba et al. describes holographic optical edge filters which have very high optical density at the laser wavelength.

Without controls such as those described, diode lasers are unstable and are thus generally regarded as of little use for Raman spectroscopic investigations. Furthermore, the wavelength of any diode laser device will gradually shift as the device ages. A diode laser device, though stable for short times, is characterized by long-term instabilities which produce a slow drift, resulting in reduced instrument reliability.

Diode lasers capable of performing at various incident wavelengths are commercially available. It is preferred to utilize a laser that has a wavelength between about 700 nm and 900 nm. Below 700 nm certain interfering background processes such as fluorescence are more prevalent than at higher wavelengths. However, wavelengths beyond 900 nm adversely affect the detection capability of currently available multichannel detection systems.

In a preferred embodiment of the method of the invention, a Raman spectrometry apparatus that includes a high powered, pigtailed, multimode diode laser that emits radiation between about 780 nm and 830 nm is employed. However, the method described in this invention is not limited to such instruments.

The large ratio of elastically to Raman scattered photons requires an efficient method of photon separation. Traditionally, this has been accomplished with double or triple spectrograph systems, constructed with two or three dispersive elements, respectively. Other radiation filtering devices can sufficiently reject the elastically scattered photons to permit the use of smaller, more efficient single dispersive element spectrograph devices; for example, holographic Bragg diffraction filters are described in Carrabba et al., *Appl. Spec.*, 1990, Vol. 44, pp. 1558–1561, the disclosures of which are incorporated herein by reference.

The detector element is highly important for proper performance of the Raman instrument and must be capable of discerning extremely low levels of radiation. Traditional scanning monochromator systems have used photomultiplier tubes that are capable of observing low photon signals. Newer instruments employ array detectors such as photodiode arrays (PDA) or charge coupled devices (CCD). Array detectors consist of multiple optical elements that can simultaneously observe a region of the spectrum up to the entire Raman spectrum. CCD detectors are multi-dimensional and able to observe multiple Raman spectra at more than one wavelength simultaneously, as described in Vess et al., SPIE, 1992, Vol. 1637, pp. 118–125, and in Angel et al., SPIE, 1991, Vol. 1587, pp. 219–231, the disclosures of which are incorporated herein by reference.

The previously mentioned paper by Wang and McCreery describes the use of a charge coupled device together with a near-infrared diode laser in a Raman spectrometer of high sensitivity. Also, Newman et al., *Appl. Spec.*, 1992, Vol. 46, pp. 262–265, the disclosures of which are incorporated herein by reference, describes the use of a CCD and diode laser with a flat field imaging spectrograph provided with a fiber optic interface with the sample.

Raman spectrometry instrumentation that combines a single dispersive grating spectrograph with a CCD detector, single-mode diode laser, fiber optic cables, a fiber optic probe, and a suitable computer is useful for rapid analytical determinations. However, mechanical stability of the spectrograph and detector system and other optical interfaces as well as the aforementioned diode laser instabilities limit the quantitative capability of the instrument. Fourier Transform (FT) Raman spectrometry has been proposed for quantitative chemical analysis. Because of instrumental variations, however, reproducibility is generally limited to, at best, about one percent, as described in Seasholtz et al., *Appl. Spec.*, 1989, Vol. 43, pp. 1067–1072.

Traditional laboratory Raman instruments use a series of lenses, mirrors, and other optics to transmit and focus the source radiation to the sample. Advances in fiber optic cables, as described, for example, in Allred and McCreery, *Appl. Spec.*, 1990, Vol. 44, pp. 1229–1231, and Schwab and McCreery, *Anal. Chem.*, 1984, Vol. 56, pp. 2199–2204, the disclosures of which are incorporated herein by reference, provide a simplified means to direct the radiation towards the sample. The simplicity, flexibility, and throughput efficiency of fiber optic cables make the prospect of remote sensing viable.

The fused silica core of the fiber optic cable, though a weak Raman scatterer, can contribute an interfering background signal when long fiber lengths are used, as discussed in U.S. Pat. No. 5,112,127; Vess et al., SPIE, 1992, Vol. 1637, pp. 118–125; Schoen et al., *Appl. Opt.*, 1992, Vol. 36, pp. 7707–7715; and Schoen et al., SPIE, 1993, Vol. 1857, pp. 116–125, the disclosures of which are incorporated herein by reference. The fundamental technique used to overcome this difficulty employs optical filters positioned near the sample. These filters remove background-inducing radiation before interferences are generated.

Fiber optic probes are typically used in conjunction with fiber optics to provide a means for transmitting radiation towards the sample and collecting the scattered radiation, as described, for example, in U.S. Pat. No. 4,573,761, the disclosures of which are incorporated herein by reference. Such probes may be constructed with combinations of fiber optics, lenses, and/or mirrors. In one construction, two or more fiber optics are secured closely together on the sample end. One or more of these fiber optics is used to transmit the radiation into the sample, and one or more additional fiber optics is used to collect and transmit the scattered radiation towards the detector.

After the scattered radiation has been collected and transmitted, it is separated using a dispersive element. The dispersion element, which is typically included along with focusing and collimating optical elements in a spectrograph, facilitates the separation of various energy levels of the scattered radiation from one another. Frequently, two or more dispersion elements are used to reject stray light more completely and increase resolution. However, there is a substantial advantage in using smaller, more efficient, single grating spectrographs with proper optical filtering, as described in the aforementioned papers of Allred and McCreery and Wang and McCreery, and also in Carrabba et al., SPIE, 1991, Vol. 1434, pp. 127–134, the disclosures of which are incorporated herein by reference. The large signal throughput increases thereby attained provide a means for extremely sensitive and reproducible measurements.

Raman spectrometry as the basis for an on-line analytical method has been discussed in several references. For example, Garrison, SPIE, 1992, Vol. 1681, pp. 291–293, describes the application of a FT-Raman system for monitoring a composition in a distillation column wherein a small stream is removed from a distillation column tray into a temperature controlled sample chamber. A Raman probe is inserted into this environment for data acquisition; the method has a relative precision of about two percent. The aforementioned paper by Seasholtz et al. describes a FT-Raman laboratory method of limited quantitative capability to develop a calibration curve for petroleum fuel products. James, PCT Int. Appl. WO87/06011 and Nguyen et al., French Patent No. 2,571,144, the disclosures of which are incorporated herein by reference, describe Raman radiation monitoring devices and methods for in situ, on-line measuring of analytical properties of a chemical or a combination of chemical components from a remote location; however there is no indication of the precision attainable by the described methods.

The method of the present invention is particularly useful for in situ monitoring of a polyester production process. Analysis of polyesters by Raman spectrometry has been known for some time; see, for example, Bulkin et al., *Macromolecules*, 1987, Vol. 20, pp. 830–835; Bower et al., *Polymer*, 1982, Vol. 23, pp. 645–649; Adar et al., *Polymer*, 1985, Vol. 26, pp. 1935–1943; and DeBlase et al., *J. Polym. Sci.*, 1985, Vol. 23, pp. 109–115, the disclosures of which are incorporated herein by reference. Typically, final product polyester materials have been investigated by off-line laboratory analyses to determine conformation, orientation, and crystallinity properties. Dramatic changes in the vibrational spectrum of the polymeric materials that correspond to processing differences have been observed. The conformation, orientation, and degree of crystallinity all affect the final product properties and usefulness for a specific application.

A typical Raman spectrum of a PET monomer sample is shown in FIG. 1. This spectrum is characterized by various peaks which are indicative of specific vibrational movements in the molecule. For example the peak located at about 1610 cm$^{-1}$ is associated with a symmetric expansion/relaxation of the terephthalate ring system. This vibrational movement is commonly referred to as a "ring breathing mode" (cf. Grasselli and Bulkin, editors, "Analytical Raman Spectrometry," vol. 14 in *Chemical Analysis*, 1991, Wiley, N.Y., pp. 223 to 252).

Vibrational movements of a molecule as measured in a Raman spectrum are specific to the molecule's nature and composition. The abundance of available structural information makes Raman spectrometry a highly desirable technique for elucidating the composition of polyesters during their formation. How to accomplish such a task in an on-line routine method is neither clear nor obvious. The goal of continuously monitoring polymer-forming compositions in the course of polyester manufacture has been achieved in the present invention. Thus, the compositional properties of any polyester, whose starting materials may include diacids and diols, diesters and diols, hydroxy carboxylic acids, hydroxy carboxylate esters, or combinations thereof, can be monitored during its synthesis in accordance with this invention.

In a Raman spectral determination, the observed signal will always be a convolution of the desired signal and an instrumental response. In general, instrumental responses broaden, shift, or otherwise distort the desired signal. The method of the present invention makes it possible to measure and compensate for both long-term and short-term variations and instabilities in the components of the Raman spectrometry apparatus. This is achieved by a referencing technique described in parent U.S. application Ser. No. 08/250,396 now U.S. Pat. No. 5,455,673, that simultaneously acquires the convolved spectra of a chemical sample in a reaction stream and a reference material, where all spectra have been subjected to the same instabilities.

The convolution process, though non-linear in an observed spectrum, can be represented as a multiplication in the time domain. FT techniques are commonly used to accomplish the conversion to and from the time domain. In the time domain, the deconvolution process is a straightforward division, using complex numbers (which consist of both a real and imaginary component), of the observed signal by the instrumental response function.

The detector continuously monitors the spectra of both a sampled chemical composition and a suitable reference material. The convolved spectrum of the reference material, also referred to herein as the convolved reference spectrum, consists of a spectral fragment with known spectral characteristics convolved with all random instabilities in the radiation source and/or mechanical instabilities in the instrument. The convolved reference spectrum is convolved by the apparatus in the same way as the convolved spectrum of the sampled chemical composition, also referred to herein as the convolved sample spectrum.

Suitable mathematical routines are also useful for the practice of this invention. The collected spectra are mathematically treated with a standardization process that compensates for all but random detector noise variability. In this process, the following spectral information is important: the convolved sample spectrum, the convolved reference spectrum, the standard reference spectrum, the standard sample spectrum, and the convolution function.

The convolved sample spectrum, $S'(x)$, is a digital representation of the Raman spectrum of the unknown sample material, as obtained from the spectrograph detector. This spectrum is influenced by variations from both instrumental (laser and/or mechanical) instabilities and structural changes in the sample.

As described above, the convolved reference spectrum, $R'(x)$, contains a spectral fragment with known shape characteristics convolved with all instrument instabilities. This spectral fragment must be convolved with the same convolution function as the convolved sample spectrum.

The convolution function, $c(x)$, which enables one to compensate for the variations resulting from radiation source variability and/or instrument mechanical instabilities, contains the information necessary to transform a standard spectrum into a convolved spectrum, and vice versa.

The standard reference spectrum, $R(x)$, is a selected spectrum that should be a true representation of the underlying shape of the convolved reference spectrum. The standard reference spectrum may be a theoretical mathematical representation of the invariant portion of the convolved reference spectrum; it may also be a previously acquired convolved spectrum of the reference material that has been adjusted or smoothed. Preferably, it is a spectrum obtained by averaging a multiplicity of previously acquired convolved spectra of the reference material. It is desirable to "linearize" the collected spectra with respect to the abscissa; this may be accomplished by various interpolation methods such as those described in W. H. Press et al., *Numerical Recipes: The Art of Scientific Computing*, 1986, Cambridge University Press, pages 77–89, the disclosures of which are incorporated herein by reference. A cubic spline interpolation described on pages 86–89 is particularly useful for this purpose. A spectrum used to provide the standard reference spectrum need not be obtained from the same instrument as that used to acquire the convolved spectra of the sample and the reference material.

Preferably, after the spectra $R'(x)$ and $S'(x)$ have been obtained, they can be transformed into the time domain using a FT method as described in, for example, *Numerical Recipes: The Art of Scientific Computing*, pp. 381–383 and 407–412, the disclosures of which are incorporated herein by reference. $R(x)$ is also transformed into the time domain and $c(x)$ is determined by dividing the FT of $R(x)$ into the FT of $R'(x)$. As the matrices for the FT of $R(x)$ and $R'(x)$ include complex numbers, this division must properly account for both the real and imaginary components.

The calculated convolution function, $c(x)$, contains the necessary information to decode the variations and instabilities of the instrument occurring during the spectral acquisition. The FT of $S'(x)$ is then divided (again both matrices contain complex numbers) with $c(x)$ to result in the FT of $S(x)$. By calculating the inverse FT on this result, a standard sample spectrum, $S(x)$, which accurately represents the composition of the sample, is obtained.

If desired, $S(x)$ may be treated by procedures to achieve curve smoothing or to obtain the spectral derivatives, for example. These procedures may be useful when the spectra are used for reproducibly extracting quantitative compositional information. Curve smoothing methods are described in A. Savitsky and M. J. E. Golay, *Anal. Chem.*, 1964, vol. 36, pp. 1627–1639.

The standard sample spectrum, $S(x)$, that is obtained in the method of the present invention is the resultant spectrum of the sampled chemical composition after all random instrument variations except random detector noise have been removed. This spectrum will vary according to chemical composition and thus enables a precise quantitative analysis of the sample.

Figure 2:
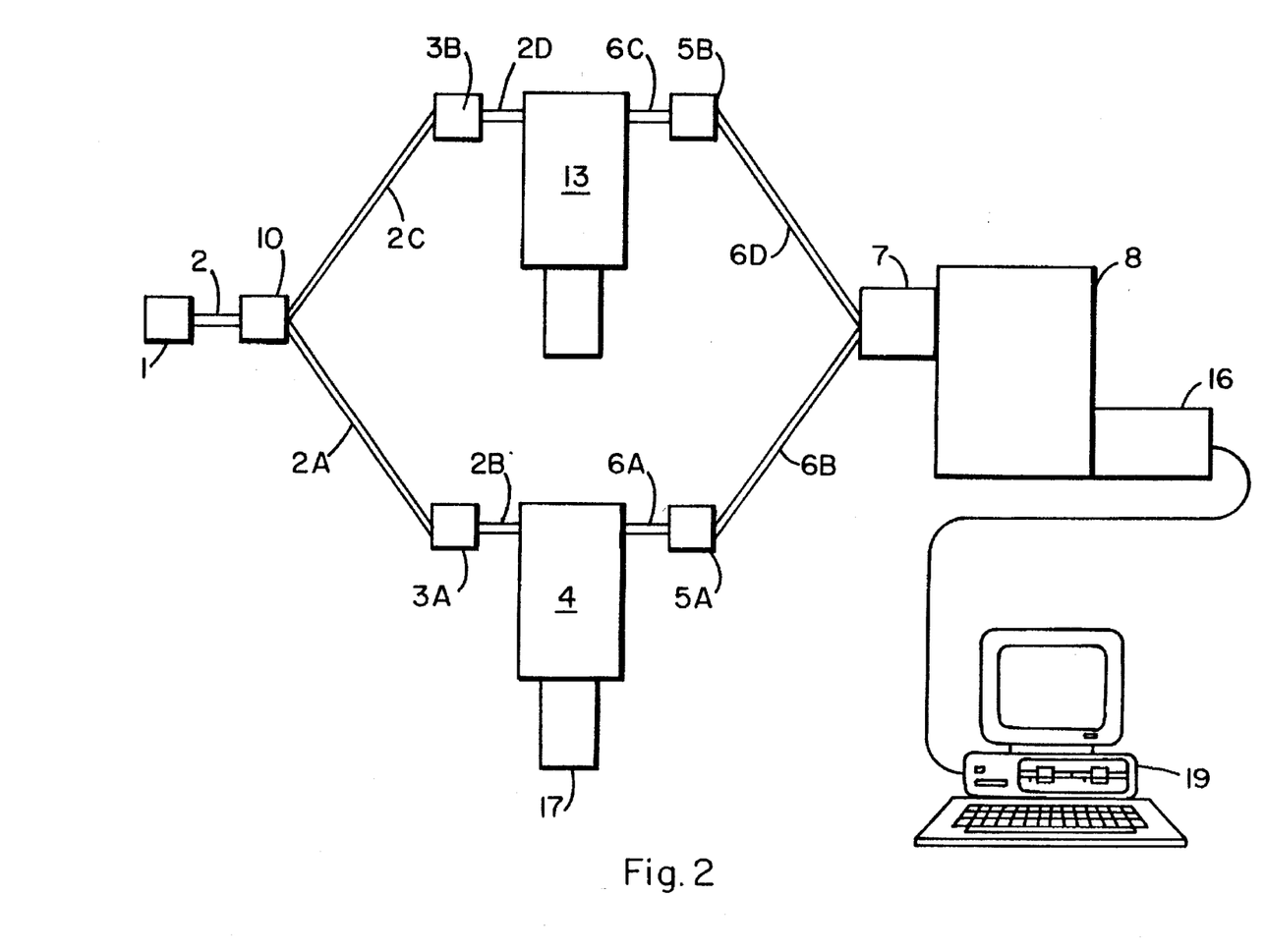
FIG. 2 is a schematic diagram of a Raman spectrometric system.

The typical Raman spectrometric system that is schematically depicted in FIG. 2 includes a radiation source 1, an optical waveguide 2, a beam splitter 10, means of transmitting the radiation to a remote sample location comprising excitation conduits 2A and 2B and 2C and 2D, radiation filters 3A and 3B, optical probes 4 and 13, radiation filters 5A and 5B, collection conduits 6A and 6B, a spectrograph interface 7, and a spectrograph 8 comprising an optical dispersion element, an array detector 16, and a computer 19 provided with appropriate mathematical routines. This system enables the simultaneous acquiring of the convolved spectra of a sample 17 and a reference material 18. The system is constructed from various components as described below.

In a preferred embodiment, the conduits 2A, 2B, 2C, 2D, 6A, 6B, 6C, and 6D, whereby radiation is transmitted to and from the sample and the reference material, comprise fiber optic cables. It is contemplated that a variety of other light transmission guides could suffice for this purpose, including combinations of optics such as mirrors, lenses, or hollow light pipes. Fiber optics that contain a fused silica core, doped fused silica cladding, and a polyamide buffer are preferred, as they provide the easiest and most efficient means of transmitting radiation in the preferred diode laser wavelength range.

As previously discussed, the use of fiber optics over long distances has an associated technical difficulty. Many of the methods previously described are sufficient to allow the use of long fibers to remote locations. A preferred method is one that is simple in construction and provides an easy means by which it can be inserted and replaced in the instrument.

In a preferred embodiment, the conduits further comprise optical filters 3A, 3B, 5A, and 5B, each of which may be situated between two small collimating lenses. These optical filter devices, which are optimized for maximum throughput, are connected to the associated excitation and collection fiber optic cables. Such optical filter devices are preferred because they are small, compact, robust, and easily removed and replaced. It is contemplated that other filtration means, described in the literature and/or commercially available, could serve the intended purpose of removal of unwanted, scattered radiation. In accordance with the present invention, the incident radiation is typically passed through band-pass filters 3A and 3B prior to entering the sample and reference material and through rejection filters 5A and 5B after collection.

The optical probes 4 and 13 that provide interfaces with the sample matter 17 of the process stream and the reference material 18 must possess the proper characteristics for the satisfactory operation of the method of the invention. At the process interface, the probe provides both for transmitting the incident radiation to the sample and collecting the scattered radiation from it. It is critical that the interface be stable under the operating conditions of the processing line; small changes at the interface can cause dramatic losses in throughput efficiencies. Chemical process conditions are often severe; for example, a polyester processing line is typically operated at temperatures between 150° and 300° C. and pressures up to 3000 psi. Such harsh conditions limit the types of materials that may be used to construct the interface.

In a preferred embodiment of the invention, a fiber optic probe constructed by soldering metal coated, fused silica fiber optic cables into a protective metal sheath, is utilized; this probe is described in copending U.S. application Ser. No. 08/450,597, filed May 25, 1995, by Buchanan et al, entitled ROBUST SPECTROSCOPIC OPTICAL PROBE, the disclosures of which are incorporated herein by reference. The probe is directly inserted into the process line and the previously described optional filter devices are connected on the opposite end of the probe tip. This probe design provides a simple, yet reliable method of optically sampling a chemical composition in a harsh physical environment of a manufacturing process. As added benefits of this design, the probe is easily removed and replaced if damage occurs, and the need for optical alignment during routine use is eliminated.

The optical dispersion element is used to separate the various energy levels of the scattered radiation. In general, the spectrograph 8 must have a suitable resolving power to separate the radiation energy levels to the desired degree. It should also be efficient to minimize loss of radiation.

Useful commercially available spectrographs are constructed with ruled gratings as the dispersion element. Depending on the size of the spectrograph box and the spacing of the lines on the grating, the instrument will have differing resolving power. Other commercially available spectrographs use specially designed holographic dispersion elements that have enhanced throughput characteristics. A preferred embodiment of the invention utilizes a single grating spectrograph with a fixed grating that disperses light such that the wavelength range 800 nm to 1000 nm is incident on the detection region. High quality instruments of this type are available from various vendors.

The array detector 16 is extremely important to effective functioning of the instrument. In order to obtain useful spectra when bubbles and particulates are in the process stream, the detector must have many closely spaced channels collecting simultaneously. Two present detection systems that are commonly used for this purpose are charge coupled devices (CCD) and photodiode arrays (PDA). CCD are preferred as these detectors have extremely low background noise levels, are extremely sensitive, and can be fashioned into two-dimensional arrays, which allow multiple spectra to be imaged on a single detector. This multiplexing capability helps to reduce the instrument cost and provides the means by which a dual beam standardization method can be utilized, as described in parent U.S. application Ser. No. 08/250,396. This standardization method increases precision and helps to reduce the cost of sampling.

CCD detection arrays are commercially available in a wide variety of shapes and sizes. Common arrays are 512 by 512 pixels and 386 by 576 pixels. Other larger array formats, such as 256 by 1024 or 1024 by 1024 pixels, are also available. Such detectors must be cooled to below room temperature to minimize interfering, background noise levels. This can be accomplished by cooling with liquid nitrogen, water, or air. Some CCD devices utilize a technology referred to as multi-pin phasing (MPP), which lowers background signal levels and noise to achieve desirable performance at temperatures lowered by air cooling.

In the preferred embodiment of the invention, it is desired to minimize noise, maximize signal, and minimize the amount of instrument maintenance required. For this reason, properly air cooled, MPP, CCD detectors are desired. A 512 by 512 pixel array is preferred because it provides adequate spectral resolution/coverage and allows for simultaneous detection of multiple channels.

The spectrograph, detector, and laser components of the spectrometric system are not generally designed to withstand the environmental effects of a production area. Therefore it is preferred to locate these devices in a safe, controlled environment, remote from the process sampling point. Optical fibers are extended between the controlled environment and the process point and connected to the optical probe, which is inserted into the process line.

Spectra collected on the described Raman spectrometric system are indicative of the chemical constitution of the material flowing within the production process. The precision and accuracy of the method is enhanced by use of the preferred embodiment of the instrumentation, although other combinations of components are also useful.

Several phenomena that can cause interferences or imprecision in the final analyses need to be understood and controlled to gain the highest possible accuracy and precision. These phenomena are: "cosmic ray" events; bubbles, particulates, and turbidity in the process; calibration point sampling; lab sampling error; and vibrations, movement, and shifting of instrumental components.

"Cosmic ray" events, often referred to as spikes, occur on CCD detectors in a random fashion. They are believed to be caused by high energy particles from outer space which, when colliding with a CCD detector element, cause a large, contaminating, spectral spike. In general, the spikes from these events are very narrow, typically 1 to 5 pixels wide. The occurrence of a cosmic ray event is rare and unpredictable, though there is some evidence that the event frequency depends on solar flare activity and the time of day.

The cosmic ray spikes are troublesome because they add a large signal in the spectrum that is not related to the process material. Fortunately, there are several simple mathematical routines that can be used to correct or despike the spectral data. One such routine is described in Takeuchi et al., Appl. Spec., 1993, Vol. 47, pp. 129–131, the disclosures of which are incorporated herein by reference.

Bubbles, particulates, and turbidity can affect the observed spectrum by obfuscating a portion of the sampled region, causing spectral intensity variations that are related to variabilities in sample volumes. Through the use of a multichannel detection system, all energy levels of the scattered radiation can be observed simultaneously. The bubbles, particulates, and turbidity act on spectral response in a manner similar to multiplication by a random number, which allows for application of a correction to normalize the spectrum. The normalization procedure, which is generally applied to the standard sample spectrum, corrects for discrepancies in the volume of material sampled by the incident radiation.

The simplest normalization scheme utilizes an internal standard that is indicative of the amount of material sampled. For PET type polyester materials, a scheme that normalizes the area of the ring breathing mode located at about 1610 cm$^{-1}$ is convenient and useful. This vibrational mode is directly related to the number of terephthalate rings sampled, enabling it to be employed for the correction of sample volume variabilities. This scheme, though preferred for its simplicity, is not the only means by which normalization can be achieved, other mathematical means by which the spectrum is normalized may be employed.

The observed Raman spectrum is a combination of vibrational bands that are related to the composition in the sampled material. However, each particular vibrational movement has a scattering efficiency which is related to the polarizability of the vibrational movement. Because of this, a simple analysis of vibrational bands will not directly provide the desired compositional information. Because no direct measure of sample composition is obtained, calibration means to relate the observed spectral characteristics to the desired analytical information must be constructed. To construct calibration means, samples correlated in time with particular acquired spectra are removed from a chemical process and analytically measured to provide chemical constitution information. Because the acquired spectra are convolved by instrumental instability, it is preferred that they be converted to standard spectra prior to construction of the calibration means. This is achieved by determining and applying a convolution function as disclosed in parent application Ser. No. 08/250,396. For this process, diamond is a preferred reference material.

Comparing at a plurality of wavelengths the Raman spectra, which are preferably standard spectra, of a plurality of chemical compositions of known constitution enables the construction of constitution-intensity correlation (CIC) multivariate calibration means. The wavelengths selected for construction of a CIC depend on the spectral characteristics of the particular component whose concentration in a chemical composition is to be determined. For each component whose in situ concentration in the composition is desired to be monitored at any given time, a separate CIC calibration is prepared.

The use and construction of calibration means, including multivariate calibration and partial least squares regression, is described in Martens et al., Multivariate Calibration, 1989, Wiley, N.Y., pages 1–6, 11–22, 25–30, 73–78, and 116–125, the disclosures of which are incorporated herein by reference. Other methods for correlating the concentrations of chemical substances with Raman spectral peak areas are described in U.S. Pat. No. 4,620,284, the disclosures of which are incorporated herein by reference.

For the preparation of PET type polymers from a mixture of dimethyl terephthalate (DMT) and ethylene glycol (EG), which may further include a limited concentration of a glycol modifier such as cyclohexanedimethanol (CHDM), it is important to monitor the extent of transesterification at various times during the process. This may be accomplished by determining the concentrations in the polymer-forming composition of methyl ester ends (from DMT), hydroxyethyl ends (from EG), and internal ethylene linkages, which are contained in the intermediate bis(2-hydroxyethyl) terephthalate (BHET). In situ determination of each of these species requires individual concentration-intensity correlations (CICs). Determining the quantity of glycol modifier present at any given time requires another CIC.

Vibrations, movements, and shifting of the various instrumental components can cause unexpected changes in the observed spectra. The types of errors induced are difficult to predict and may cause inaccuracies that result in limited precision. It is therefore important to eliminate or minimize the effects of vibrations, movements, and shifting in the instrument, which can be "hardened" by a robust assembling of its components in a sturdy construction. The better hardened an instrument, the higher precision it will ultimately be capable of attaining.

Sample probes may be placed at any location in a chemical manufacturing process stream, but it is generally advisable to place a probe in a location where it will provide information that is useful for controlling the process and for providing analytical information for calibration purposes.

One preferable sample probe location in a polyester production process is near the point in the process where the first stage reaction is near completion. This provides a means by which analytical information regarding extent of reaction, mole ratio of diols to acids and or diesters, percent of diol or diacid modifiers, and degree of polymerization can be quickly ascertained. Such information allows for improved control of the first stage of the process and improves downstream control.

The following examples further illustrate the invention.

EXAMPLE 1

Demonstration of Method Capability in a Batch Process

The technical capability of the monitoring method was demonstrated in a laboratory reaction vessel under conditions similar to those of a production process environment. The transesterification reaction of DMT and EG was continuously monitored in situ by Raman spectroscopy as samples were removed periodically from the vessel. A second, subsequent reaction run was used to compare the Raman estimated data to the NMR measured data and demonstrate thereby the validity of the calibration.

A Raman instrument was constructed containing a krypton ion gas laser (from Lexel, Fremont Calif.), operating at 752 nm, as a radiation source. The plasma lines from the lasing process were filtered from the incident radiation beam by a dielectric band pass filter as the radiation was focused onto a 200 micrometer core, polyimide buffered, fused silica fiber optic cable. The fiber optic transmitted the radiation to a sample probe which was inserted directly into the reaction medium.

The scattered radiation was collected by six 200 micrometer fibers positioned closely about the excitation fiber. The six collection fibers were directed back towards an Instruments SA (Edison, N.J.) model 320 spectrograph. The fibers were arranged into a linear array and positioned directly in front of the entrance optics.

The entrance optics served first to collimate the radiation, then pass it through a Kaiser Optics (Ann Arbor, Mich.) holographic-band rejection filter that eliminated virtually all elastically scattered radiation, and finally to focus the filtered radiation onto the entrance slit of the spectrograph. The dispersed light was detected by an ISA liquid nitrogen cooled CCD detector and converted into an electronic signal.

The instrument was controlled by software that permitted continual collection of sequential data files. Pairs of 30-second sequential spectra were acquired and compared to remove cosmic spike events. Following spike removal, the two spectra were averaged. The aromatic ring breathing vibration spectral feature at 1610 cm$^{-1}$ was used as the convolved reference spectrum for the standardization process disclosed in parent U.S. application Ser. No. 08/250,396 to remove band shape and band position variations. The area of the aromatic ring breathing mode at 1610 cm$^{-1}$ was used for normalization.

The resultant, standardized waveform was smoothed in the Fourier domain by a three point halfwidth Gaussian broadening function and a one-point halfwidth Lorenztian narrowing function. The second derivative of the data was calculated and the resultant standardized, smoothed data was used to construct a CIC calibration, using a partial least squares (PLS) data analysis package (UNSCRAMBLER from Computer Aided Modelling A/S of Trondheim, Norway).

Approximately 1065 grams of DMT and 865 grams of EG were added to a large reaction vessel. A specially designed lid with fittings for an optical probe, thermocouple, stirrer, condenser, and sample port was attached. A gentle stream of clean nitrogen was passed above the reaction mixture to blanket the mixture against oxygen.

The reaction mixture was carefully heated to 180° C. as Raman spectra were being acquired. After collection of a few baseline spectra, approximately 0.20 grams of manganese acetate catalyst was inserted into the mixture. After a few hours, the reaction temperature was raised to 195° C., and after another period of time, raised to 210° C.

At intervals during the reaction, a sample was removed and analyzed by NMR spectrometry to determine the number of aromatic terephthalate rings, referred to as -T-; methyl ester ends, referred to as —CH$_3$; hydroxyethyl ends, referred to as —OH; internal ethylene linkages, referred to as -2-; and free EG.

Figure 3:
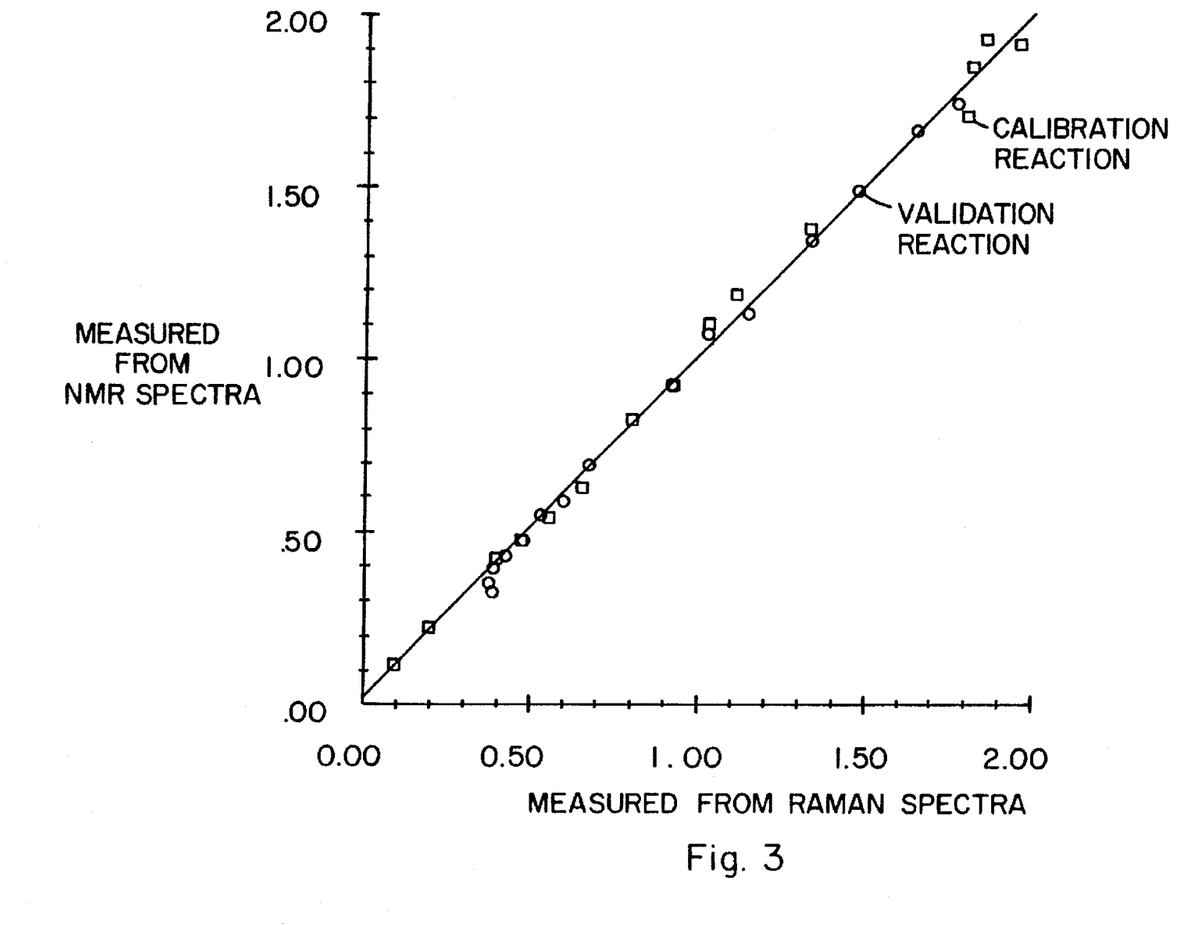
FIG. 3 is a correlation plot for determining methyl ends in a polymer-forming composition.

FIG. 3 shows the calibration and validation reaction values for the number of methyl ends. The number of measured methyl ester ends, —CH$_3$ was normalized to the terephthalate rings, -T-, giving a direct measure of the extent of the transesterification reaction. This calibration curve exhibits a correlation coefficient of 0.9999, indicating that the Raman method is very capable of determining the analytical results required over the entire compositional range of the transesterification reaction.

Figure 4:
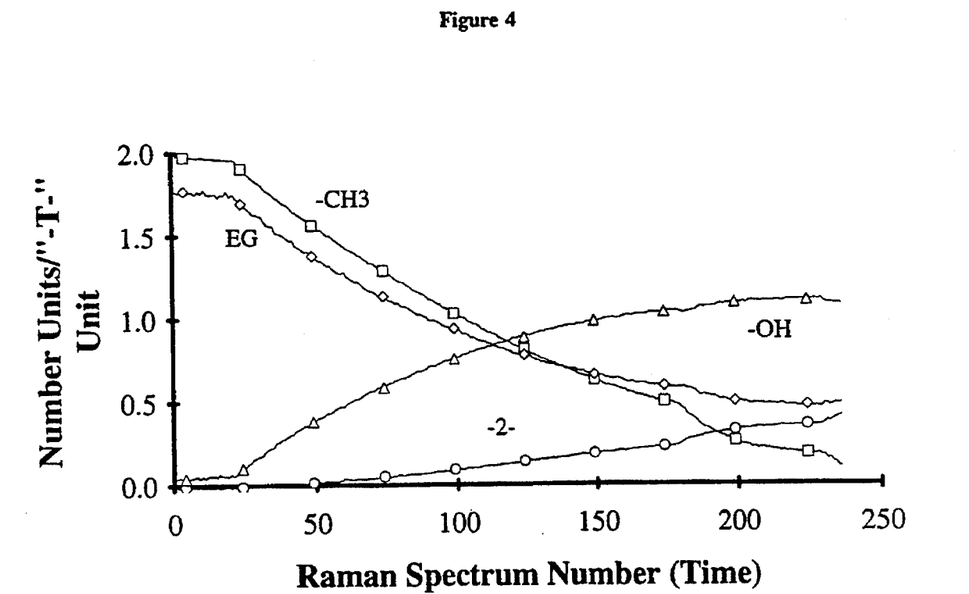
FIG. 4 is a graph summarizing the kinetics of the reaction of dimethyl terephthalate with ethylene glycol.

FIG. 4 shows a plot of various parameters measured throughout the reaction. Individual spectra were acquired approximately once per minute. The initial 20 minutes were obtained with the vessel at 180° C. and no catalyst present. After the catalyst was added, the reaction increased rapidly. After three hours (spectrum number 180), the reaction temperature was raised to 195° C., and after four hours (spectrum number 230), the temperature was further raised to 210° C.

The data in FIG. 4 demonstrate the exceptional ability of the invention for determining several important components in the reaction. The number of methyl ester ends is indicative of the extent of formation of the intermediate BHET and is an important criterion for good polymer manufacture. The internal ethylene units are directly related to the degree of polymerization and molecular weight, which are other important properties.

EXAMPLE 2

Analysis in a Polyester Production Reaction Stream

To demonstrate the utility of the invention as an in situ, on-line, quantitative analytical tool in a production environment, a Raman instrument was installed near a polyester production line. A robust probe, constructed as disclosed in the aforementioned copending U.S. application Ser. No. 08/450,597, filed May 25, 1995, entitled ROBUST SPECTROSCOPIC OPTICAL PROBE, was installed so that the sampling tip protruded into the flowing, molten, polyester stream. The particular process line was designated to manufacture a glycol modified PET produced from DMT, EG, and CHDM. The measurement process was demonstrated over a six week period. Analytical data corresponding to the extent of the first stage (transesterification) reaction, mole ratio of glycols to acids, and percent composition of the CHDM glycol modifier were obtained.

The Raman instrument was constructed to include a 2.0 Watt multimode diode laser operating with 800 nm excitation; this was pigtailed to a 100 micrometer silica quartz core, fiber optic cable (Spectra Diode Lab, Inc., San Jose, Calif. model number SDL-2372-P3). The incident radiation was split into two beams with a fiber optic beam splitter (Oz Optics Ltd., Carp, Ontario, Canada, model number FOBS-12-555-MMM-750-50/50). Both beams were focused onto individual 200 micrometer core, polyimide buffered, quartz silica fiber optic cable (Fiberguide Industries, Stirling, N.J.). The two fiber optics transmitted the radiation to both a sample probe and a reference probe. The sample probe was inserted directly into the process stream some 40 meters distant.

The radiation in each fiber optic cable was filtered prior to entering the individual probes. The filters were designed to transmit only a narrow energy band (Omega Optical, Brattleboro, VT model number 800 BP10) and were inserted into fixed fiber optic filter holding device (Oz Optics, Ltd. model number ND-200-55-750-M-30). The reference probe was used to illuminate a small diamond fragment, which was used as a reference material. The sample probe was inserted through a flange port into the process stream.

The scattered radiation from both reference and sample was collected by individual 200 micrometer fibers positioned closely about the excitation fibers. The collected scattered radiation was filtered to remove nearly all of the Rayleigh scattered radiation prior to entering the return fiber. The filter (Omega Optical, model number 800 REFLP) was held in a fixed fiber optic filter holding device (Oz Optics, Ltd- model number ND-200-55-750-M-30) and was designed for efficiently rejecting the unwanted radiation while allowing collection of the desired Raman scattered radiation.

Both return fibers were directed back towards an ISA 320 spectrograph. The fibers were arranged into a linear array and positioned directly in front of the entrance slit. The dispersed light was detected by an ISA liquid nitrogen cooled CCD detector and converted into an electronic signal.

The instrument was controlled with software that permitted continual collection of sequential data files. Pairs of 30-second sequential spectra were acquired and compared to remove cosmic spike events, and the two despiked spectra were averaged. A cubic spline interpolation as described in *Numerical Recipes: The Art of Scientific Computing*, pages 86–89, the disclosures of which are incorporated herein by reference, was used to provide equally spaced abscissa data in the convolved reference and sample spectra. Standardization and normalization were carried out as described in Example 1. The resultant standardized waveform was smoothed in the Fourier domain by a nine-point halfwidth Gaussian broadening and a seven-point halfwidth Lorenztian narrowing function. Five sequential smoothed standardized waveforms were averaged together to provide one data point every 5 minutes.

The sample probe was located in the process stream at a location where the transesterification reaction was assumed to be nearly complete. The temperature was approximately 235° C. and the pressure approximately 30 psig inside the process environment. A sample port was located within a few feet of the sample probe, and a small sample of the oligomer was removed once every 12 hours. This sample was analyzed by NMR to determine the extent of the transesterification reaction.

The second derivative, standardized smoothed spectra that corresponded in time to the analyzed compositions of known concentration were used to construct a CIC calibration. Calibrations were constructed using a partial least squares (PLS) data analysis package (UNSCRAMBLER from Computer Aided Modelling A/S of Trondheim, Norway).

Figure 5:
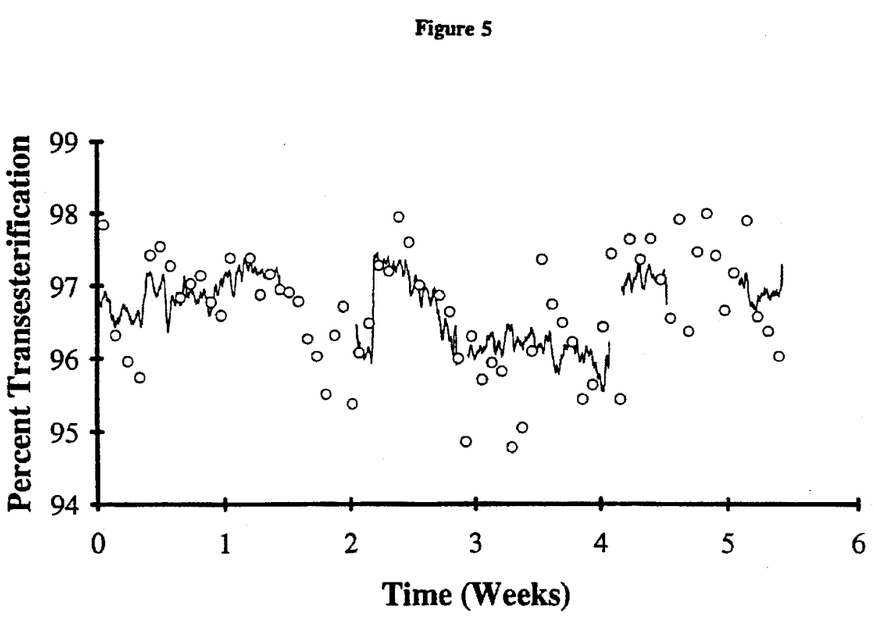
FIG. 5 is a graph comparing Raman and NMR spectrometric analytical data for a polyester production line.

FIG. 5 shows the NMR results from the extracted samples (shown as open circle marker points) and data obtained with the Raman instrument (shown as a solid line) over an approximate six week period for the extent of the transesterification reaction. The NMR data indicate a widely varying process where the point to point deviation is the predominant trend in the data. The major sources of variation are presumably caused by sample removal, inherent process variations, and the analytical measurements.

Discontinuities in the Raman data were caused by either failure to refill the liquid nitrogen container or accidental loss of data.

A statistical analysis of the process data confirmed the observation that the Raman data has much less point-to-point variation than the NMR measurements. The Raman method demonstrated excellent relative precision, about 0.1%. The greatest source of variance in the NMR data was in the sampling method, not surprising considering the manner in which samples were removed from the process.

In addition to higher precision, the Raman method clearly provides more frequent sampling, diminished sample removal requirements, and much faster turn-around times than the NMR analysis. More frequent sampling provides a means to better understand the nature and duration of true variations in the process. The decreased need to remove samples dramatically decreases the risk of injuries. The faster turn-around time provides a means by which a more active process control strategy can be obtained. The use of this invention clearly enables more frequent and precise measurement of the variables.

EXAMPLE 3

Demonstration of Method Capability for Mixed Xylenes

The technical capability of the method to determine the constitution of other chemical compositions was demonstrated by preparing a sample set of mixed xylenes. The samples were prepared by carefully weighing varying amounts of each component into the mixture. The molar concentration percentages were calculated and used as the actual values, shown as STD in Table 1 below.

The Raman instrument was constructed to contain a 2.0 Watt multimode diode laser operating with 800 nm excitation that was pigtailed to a 100-μm silica quartz core, fiber optic cable (Spectra Diode Lab, Inc., San Jose, Calif. model number SDL-2372-P3). The incident radiation was split into two beams with a fiber optic beam splitter (Oz Optics Ltd., Carp, Ontario, Canada, model number FOBS-12-555-MMM-750-50/50). Both beams were focused onto individual 200-μm core, polyimide buffered, quartz silica fiber optic cable (Fiberguide Industries, Stirling, N.J.). The two fiber optics transmitted the radiation to both a sample probe and a reference probe.

The radiation in each fiber optic cable was filtered prior to entering the individual probes. The filters were designed to transmit only a narrow energy band (Omega Optical, Brattleboro, VT model number 800 BP10) and were inserted into fixed fiber optic filter holding device (Oz Optics, Ltd. model number ND-200-55-750-M-30).

Both the reference and the sample fiber optic probes were constructed in-house. The reference probe was used to illuminate a small diamond fragment, which was used as a reference material. The sample probe was inserted into a 316 stainless steel sample tube in which the mixed xylene samples were placed.

The scattered radiation from both reference and sample was collected by individual 200-μm fibers positioned closely about the excitation fibers. The collected scattered radiation was filtered to remove nearly all of the Rayleigh scattered radiation prior to entering the return fiber. The filter (Omega Optical, model number 800 REFLP) was held in a fixed fiber optic filter holding device (Oz Optics, Ltd. model number ND-200-55-750-M-30) and was designed to efficiently reject the unwanted radiation, while passing the desired Raman scattered radiation.

Both return fibers were directed back towards an Acton SpectraPro spectrograph (Acton Research Corporation, Acton, Mass.). The monochromator was constructed with a turret-style grating system with three dispersive gratings. These gratings were: 150 grooves/mm, blazed at 750 nm;

300 grooves/mm, blazed at 750 nm; and 600 grooves/mm, blazed at 750 nm. The 300 grooves/mm grating was used for the analysis and provided approximately 1700 cm$^{-1}$ spectral coverage.

A fiber adapter fashioned with eight 200-μm inputs was connected at the entrance of the monochromator to enable eight Raman channel collection. The fibers were arranged into a linear array and positioned directly in front of the entrance slit. One of these eight monochromator fibers was connected to the sample probe fiber and another was connected to the reference probe fiber. The dispersed radiation was detected by a Princeton Instruments (Trenton, N.J.) thermoelectric-cooled CCD detector and converted into an electronic signal. The CCD chip was a Techtronix 512 by 512 pixel, back-illuminated detection system.

The instrument was controlled with the CSMA data acquisition software provided by Princeton Instruments; 30-second spectra were acquired. A cubic spline interpolation was applied as in Example 2 to linearize the convolved reference and sample spectral data with respect to the abscissa. The standardization process described in parent U.S. application Ser. No. 08/250,396 was applied to remove band shape and band position variations. The resultant standardized waveform was smoothed in the Fourier domain by a three point half width, Gaussian broadening and two point half width, Lorenztian narrowing function.

The standard sample spectra from samples A–K were used in conjunction with a partial least squares (PLS) data analysis package (UNSCRAMBLER from Computer Aided Modelling A.S of Trondheim, Norway) to generate a calibration for each component of the xylene mixture. This calibration was used to provide the composition information from each sample.

Samples L–Q constitute an independent validation set. These samples were measured in a similar fashion to samples A–K, which provided a standard spectrum for each sample. The calibration function was applied to each standard spectrum to provide a measure of sample composition.

The monochromator center was intentionally shifted from 901 nm to 899 nm to simulate an instability in the apparatus, and samples G and L–Q were measured again (relabeled as samples R–X) to provide a new set of standard spectra. The calibration function was applied to each standard spectrum to provide a measure of sample composition.

In Table 1 below are shown, in the column labeled "Invention", the composition in molar percentage of the xylene mixtures as determined from their Raman spectra by the method of the present invention. The discrepancies between these values and the actual percentages, listed in the "STD" column, as shown in the "Difference" column. The components are identified as follows:

P=para-xylene, M=meta-xylene, and O=ortho-xylene.

TABLE 1

| Sample | Component | STD | Invention | Difference |
| --- | --- | --- | --- | --- |
| A | P | 39.86 | 39.84 | −0.02 |
|   | M | 35.22 | 35.19 | −0.03 |
|   | O | 24.91 | 24.97 | 0.06 |
| B | P | 39.98 | 40.10 | 0.12 |
|   | M | 25.01 | 25.07 | 0.06 |
|   | O | 35.01 | 34.83 | −0.18 |
| C | P | 34.97 | 34.99 | 0.02 |
|   | M | 25.13 | 25.21 | 0.08 |
|   | O | 39.91 | 39.80 | −0.11 |
| D | P | 34.78 | 34.81 | 0.03 |

TABLE 1-continued

| Sample | Component | STD | Invention | Difference |
| --- | --- | --- | --- | --- |
|   | M | 39.93 | 39.94 | 0.01 |
|   | O | 25.29 | 25.25 | −0.04 |
| E | P | 39.95 | 39.83 | −0.12 |
|   | M | 25.08 | 24.92 | −0.16 |
|   | O | 34.97 | 35.25 | 0.28 |
| F | P | 33.34 | 33.28 | −0.06 |
|   | M | 33.32 | 33.44 | 0.12 |
|   | O | 33.33 | 33.28 | −0.05 |
| G | P | 33.42 | 33.51 | 0.09 |
|   | M | 33.23 | 33.11 | −0.12 |
|   | O | 33.35 | 33.37 | 0.02 |
| H | P | 25.12 | 25.14 | 0.02 |
|   | M | 39.94 | 39.91 | −0.03 |
|   | O | 34.94 | 34.95 | 0.01 |
| I | P | 35.04 | 35.05 | 0.01 |
|   | M | 39.97 | 39.93 | −0.04 |
|   | O | 24.99 | 25.02 | 0.03 |
| J | P | 39.97 | 39.93 | −0.04 |
|   | M | 35.01 | 35.11 | 0.10 |
|   | O | 25.02 | 24.95 | −0.07 |
| K | P | 24.97 | 24.92 | −0.05 |
|   | M | 35.09 | 35.11 | 0.02 |
|   | O | 39.95 | 39.97 | 0.02 |
| L | P | 30.14 | 30.16 | 0.02 |
|   | M | 29.92 | 29.92 | 0.00 |
|   | O | 39.94 | 39.92 | −0.02 |
| M | P | 30.03 | 30.07 | 0.04 |
|   | M | 39.90 | 39.82 | −0.08 |
|   | O | 30.07 | 30.12 | 0.05 |
| N | P | 39.96 | 39.96 | 0.00 |
|   | M | 29.95 | 30.07 | 0.12 |
|   | O | 30.09 | 29.97 | −0.12 |
| O | P | 35.01 | 34.85 | −0.16 |
|   | M | 35.03 | 34.89 | −0.14 |
|   | O | 29.97 | 30.26 | 0.29 |
| P | P | 35.00 | 35.12 | 0.12 |
|   | M | 30.01 | 29.90 | −0.11 |
|   | O | 34.99 | 34.98 | −0.01 |
| Q | P | 30.03 | 30.04 | 0.01 |
|   | M | 34.99 | 35.00 | 0.01 |
|   | O | 34.98 | 34.97 | −0.01 |
| R | P | 33.42 | 33.40 | −0.02 |
|   | M | 33.23 | 33.15 | −0.08 |
|   | O | 33.35 | 33.45 | 0.10 |
| S | P | 30.14 | 30.12 | −0.02 |
|   | M | 29.92 | 29.76 | −0.16 |
|   | O | 39.94 | 40.12 | 0.18 |
| T | P | 30.03 | 29.91 | −0.12 |
|   | M | 39.90 | 40.08 | 0.18 |
|   | O | 30.07 | 30.01 | −0.06 |
| U | P | 39.96 | 39.79 | −0.17 |
|   | M | 29.95 | 29.88 | −0.07 |
|   | O | 30.09 | 30.33 | 0.24 |
| V | P | 35.01 | 34.92 | −0.09 |
|   | M | 35.03 | 35.03 | 0.00 |
|   | O | 29.97 | 30.05 | 0.08 |
| W | P | 35.00 | 35.05 | 0.05 |
|   | M | 30.01 | 30.15 | 0.14 |
|   | O | 34.99 | 34.80 | −0.19 |
| X | P | 30.03 | 29.86 | −0.17 |
|   | M | 34.99 | 35.07 | 0.08 |
|   | O | 34.98 | 35.07 | 0.09 |

In Table 2 below are shown the standard errors of calibration for mixtures A–K and of prediction for the sets of mixtures L–Q and R–X as determined, in accordance with the invention, by applying a convolution function to the measured Raman spectra of the samples. Included for comparison in Table 2 are the values for the errors of calibration and prediction absent the application of the method of the present invention.

TABLE 2

| Standard Error | Comparison | | | Invention | | |
|---|---|---|---|---|---|---|
| | P | M | O | P | M | O |
| Samples A–K | 0.225 | 0.191 | 0.338 | 0.066 | 0.084 | 0.110 |
| Samples L–Q | 0.336 | 0.329 | 0.591 | 0.082 | 0.096 | 0.134 |
| Samples R–X | 3.595 | 3.949 | 7.495 | 0.109 | 0.116 | 0.148 |

From the entries of Table 2 it is clear that the invention provided a substantial reduction in the standard error values even for the calibration sample set A–K. The improvement was even greater with the validation sample set L–Q. However, it was in the case of set R–X, where the monochromator center was intentionally shifted by 2 nm in simulation of spectrophotometric system instability, that the method of the invention demonstrated its benefit most strikingly, producing a dramatic reduction in the standard errors of prediction.

The invention has been described in detail with particular reference to preferred embodiments thereof, but it will be understood that variations and modifications can be effected within the spirit and scope of the invention.

What is claimed is:

1. A method for quantitatively monitoring in situ by Raman spectrometry one or more selected constituents of a chemical composition, which comprises:

(a) simultaneously irradiating with a substantially monochromatic radiation source a reference material and a chemical composition comprising one or more chemical constituents, said radiation being transmitted from said source to an optical probe that interfaces with said chemical composition, said source being connected to said probe by means of an excitation conduit;

(b) simultaneously acquiring at more than one wavelength a convolved Raman spectrum of said reference material and a convolved Raman spectrum of said chemical composition by means of a spectrograph remotely situated from said chemical composition, said spectrograph being connected to said optical probe by means of a collection conduit;

(c) choosing a standard Raman spectrum of said reference material;

(d) from said convolved Raman spectra and said standard Raman spectrum of said reference material, determining a convolution function;

(e) applying said convolution function to adjust said convolved Raman spectrum of said chemical composition to produce thereby a standard Raman spectrum of said chemical composition; and (f) applying predetermined calibration means to said standard Raman spectrum of said chemical composition;

whereby the quantity of one or more selected constituents of said chemical composition at the time of the acquiring of said convolved Raman spectra can be ascertained.

2. A method according to claim 1 wherein said source of radiation is a laser.

3. A method according to claim 2 wherein said laser is a diode laser.

4. A method according to claim 3 wherein said diode laser is a multi-mode diode laser.

5. A method according to claim 1 wherein said spectrograph is a dispersion spectrograph or a FT-interferometer.

6. A method according to claim 1 wherein said reference material comprises diamond.

* * * * *